United States Patent [19]

Bailey et al.

[11] Patent Number: 4,710,217

[45] Date of Patent: Dec. 1, 1987

[54] BONDING GLASS-CERAMIC DENTAL PRODUCTS

[75] Inventors: Lorraine F. Bailey, Painted Post, N.Y.; Richard J. Bennett, Milford, Del.

[73] Assignee: Corning Glass Works, Corning, N.Y.

[21] Appl. No.: 837,729

[22] Filed: Mar. 10, 1986

[51] Int. Cl.[4] .......................... C03C 17/00; A61C 5/08
[52] U.S. Cl. ........................................ 65/31; 156/663; 156/654; 433/219
[58] Field of Search ................... 65/31, 36, 42, 43, 58, 65/901; 156/625, 629, 663, 633, 654; 433/219, 223

[56] References Cited

U.S. PATENT DOCUMENTS

| | | | |
|---|---|---|---|
| 4,215,033 | 7/1980 | Bowen | 65/31 |
| 4,376,673 | 3/1983 | Cheung | 156/663 |
| 4,376,835 | 3/1983 | Schmitt et al. | 156/663 |
| 4,380,432 | 4/1983 | Orlowski et al. | 433/219 |
| 4,431,420 | 2/1984 | Adair | 501/3 |

*Primary Examiner*—S. Leon Bashore
*Assistant Examiner*—Michael K. Boyer
*Attorney, Agent, or Firm*—C. S. Janes, Jr.

[57] ABSTRACT

The present invention is directed to a method for developing a bond having a shear strength in excess of 1200 psi between dental cements and dental appliances fashioned from glass-ceramic materials. The inventive method consists of contacting the fitting surface of the appliance with an etchant in flowable gel form at a temperature below about 150° F., while protecting the exterior surface of the appliance. Subsequently, a silane solution followed by a dental cement is applied to the etched surface and cured in place.

8 Claims, 2 Drawing Figures

BONDING GLASS-CERAMIC DENTAL PRODUCTS

BACKGROUND OF THE INVENTION

The fabrication of thin veneers for labial placement on discolored anterior teeth has been practiced by dental laboratories for a number of years. In general, the application of veneers has required a thin sheet of a ceramic material or of an organic resin (~0.5–0.75 mm in thickness) to be cast, the sheet shaded to be compatible in color with adjacent teeth, and then cemented to the patient's tooth. As can be appreciated, considerable research has been conducted in devising cements to insure high shear bonding between the tooth and the veneer element.

In a rather recent development, dental laboratories have fabricated dental appliances or prostheses (inlays, onlays, crowns, bridges, veneers, etc.) from glass-ceramic materials. Various compositions have been employed, the most common having a calcium phosphate or a fluormica as the predominant crystal phase. Thus, glass-ceramic materials have been designed demonstrating high mechanical strength, a coefficient of thermal expansion and a thermal conductivity approximating those of tooth enamel, a level of translucency such as to impart a visual appearance similar to that of tooth enamel, excellent resistance to food staining and chemical attack in an oral environment, and a ready capability of being shaded to a desired coloration.

It has been recognized that a stronger bond can be obtained between a cement and the substrate to which the cement is applied by increasing the surface area of the substrate in the region where the cement is to be applied. Such increase in surface area can be secured by roughening the substrate surface through such means as sandblasting. A more carefully controllable process contemplates differential etching. To be effective, as can be appreciated, differential etching requires the presence of at least two different phases in the body which react at markedly unequal rates when subjected to the etchant.

As is recognized in the art, a glass-ceramic body consists of crystals dispersed within a residual glassy matrix, the crystals customarily comprising the greater proportion of the body and having a composition substantially different from that of the residual glass. Because of this significant difference in composition existing in the crystal phase vis-a-vis the glass phase, an etchant which would remove the glass phase much more rapidly than the crystals would yield holes in the surface which would extend inwardly into the body. Such holes would not only substantially increase the surface area, but also the tortuous path which the etchant would produce in removing the glass phase around the crystals would provide improved bonding for cement applied thereto through a form of mechanical interlocking. The reverse process, i.e., the etching of the crystals with the glass phase being left in place, is also, of course, possible. However, insasmuch as the crystals normally constitute the greater phase in glass-ceramics, their removal may leave a weakened body.

Because the interior fitting surface of a dental appliance could require etching prior to being cemented to the surface of a patient's tooth, some constraints are necessarily placed upon the etching process. For example, inasmuch as the etching procedure would be conducted on the finished appliance, e.g., a shaded veneer, the finished surface must be protected during the etching. The temperature of the etching treatment should not exceed about 150° F. (~65° C.). A stronger bond between the etched appliance and the cement than between the etched tooth enamel and the cement will desirably be provided. In general, the bond strength of organic polymers to etched tooth enamel is on the order of 1200 psi.

Therefore, the primary objective of the present invention was to devise a method for developing a bond between dental cements (organic polymer adhesives) and etched appliances prepared from glass-ceramic compositions exhibiting bond strengths in excess of 1200 psi.

Another important objective of the present invention was to devise an etching procedure which would be conducted on finished, shaded glass-ceramic dental appliances that could be carried out at temperatures not exceeding about 150° F., and wherein the finished surface of the construct would be protected during the etching process.

SUMMARY OF THE INVENTION

We have found those objectives can be achieved through a five-step process:

(a) the internal or fitting surface of a dental appliance prepared from a glass-ceramic material is contacted with an etchant in gel form for a period of time sufficient to promote etching of the surface to provide a bonding surface having a depth of about 0.25–5 microns with holes having diameters of about 0.25–10 microns dispersed throughout the bonding surface;

(b) the gelled etchant is removed from the internal surface of the dental appliance;

(c) the etched surface of the dental appliance is contacted with a silane solution for a sufficient length of time to insure satisfactory impregnation of the etched holes in the construct surface therewith;

(d) the excess silane solution is removed from the etched surface of the appliance and that remaining in the holes dried and cured (the cure may optionally be undertaken at elevated temperatures or through a chemical reaction); and (e) a dental cement is applied to the etched surface and cured in place.

The most preferred glass-ceramic materials for dental appliances comprise those disclosed in U.S. Pat. No. 4,431,420. Those glass-ceramics have compositions consisting essentially, expressed in terms of weight percent on the oxide basis, of 10–18% $K_2O$, 14–19% MgO, 0–2% $Al_2O_3$, 0–7% $ZrO_2$, 55–65% $SiO_2$ and 4–9% F; and contain tetrasilicic fluormica as the predominant crystal phase in the interior of the body with a surface containing non-fluoride crystals identified as enstatite ($MgSiO_3$).

GENERAL DISCUSSION

To simulate veneer configurations, rectangular bars having dimensions of about 20 mm×11 mm×3 mm were prepared from a glass-ceramic coming within the description of U.S. Pat. No. 4,431,420 and having the following approximate composition: 14% $K_2O$, 17% MgO, 0.5% $Al_2O_3$, 5% $ZrO_2$, 58.5% $SiO_2$, and 5% F. The bars were subjected to a light blast of air in the range of about 40–80 psi containing particles of $Al_2O_3$ having diameters of about 25 microns (grit blast), cleaned ultrasonically, and then dried.

In the description reported below, bars exposed to different treatments were subjected to the following test procedures to measure the shear bond strength between the dental cement and the bar.

(1) Dental cement was introduced into a section of a plastic drinking straw, 4–5 mm in length with a 3.654 mm I.D., such that about 3 mm of the cement was present in one end of the straw.

(2) The end of the straw containing the cement was placed into contact with a surface of the bar. Thereafter, the cement-containing end of the straw was pinched between fingers to flow the cement out onto the surface of the bar into a post-like configuration. Two sides of the bar were so contacted in order to produce a second post and thereby provide two data points.

(3) The coated bar was then stood upright and the cement cured. Depending upon the cement employed, the curing consisted of a 60 second exposure to high intensity visible light, a self cure through exposure to a temperature of 37° C., or a combination of both.

(4) The bar was immersed into a bath of distilled water operating at 37° C. for a specified length of time.

Figure 1:
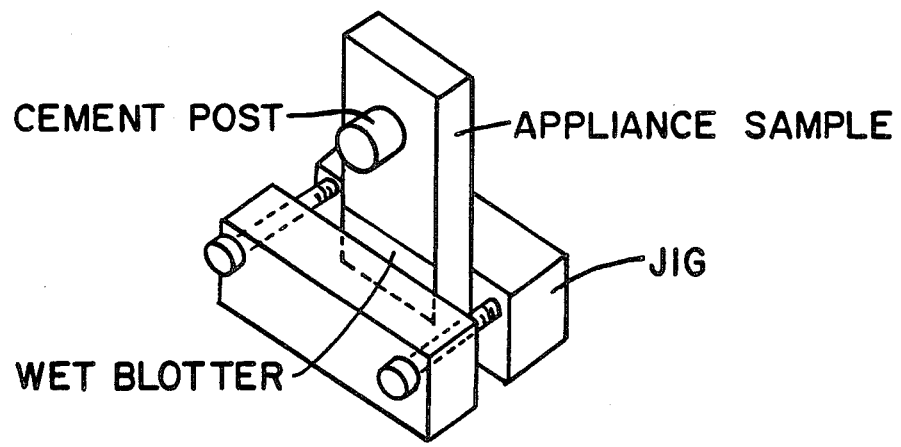
FIG. 1 comprises an isometric view schematically depicting the jig apparatus used to hold samples for testing.

(5) The bar was transferred from the bath to the holding jig pictured in FIG. 1; wet blotter paper being used to protect the bar from the jaws of the jig.

Figure 2:
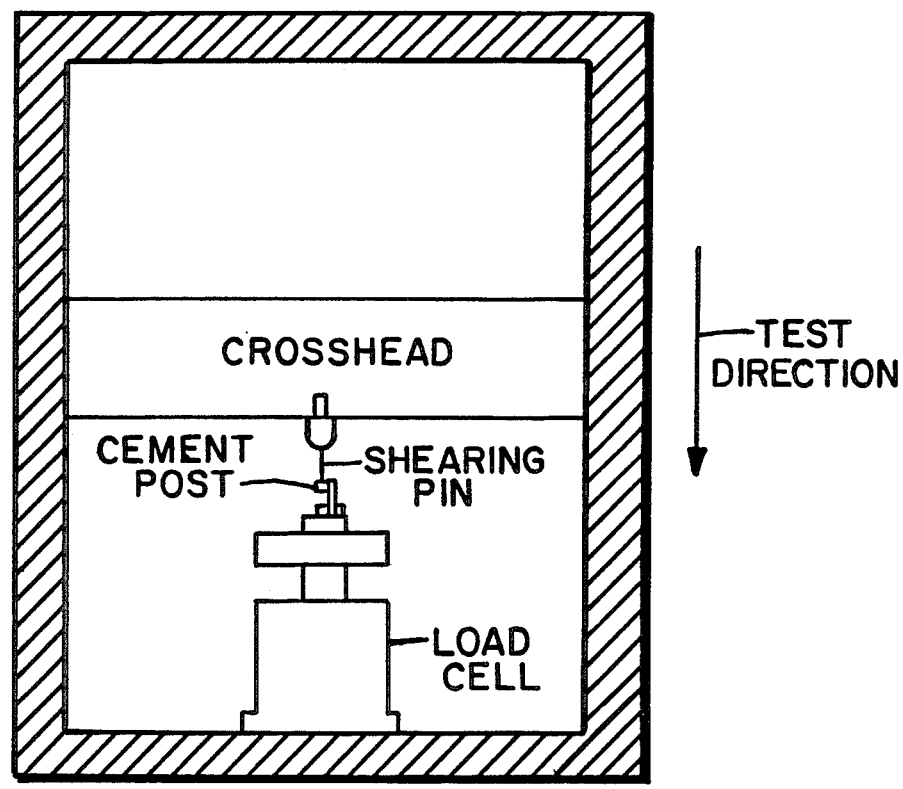
FIG. 2 schematically illustrates the test configuration used in subjecting a sample to shear compression.

(6) The jig was placed in an Instron testing machine operating in the shear compression mode. The test configuration is schematically illustrated in FIG. 2. As can be observed, the shearing pin was positioned to be almost in contact with the cement post.

(7) The testing machine was programmed at a crosshead speed of 5 mm/minute, a chart speed of 200 mm/minute, and a maximum load of 50 kg.

(8) The testing machine was made operational, the specimens debonded, the point of failure observed, and the percent of the maximum load recorded.

To investigate the effectiveness of various types of etchants, initial laboratory experimentation employed the following three solutions:

(a) STRIPIT, a commercial solution of HF and $H_2SO_4$ marketed by National Keystone Products Company of Philadelphia, Pennsylvania, and currently utilized in the dental industry for etching porcelain veneers. An analysis of STRIPIT indicated an aqueous solution containing 5.4% HF and 6.5% $H_2SO_4$.

(b) An aqueous solution containing 10% NaOH and 1% EDTA.

(c) An aqueous solution containing 5% HCl.

A two minute exposure at room temperature was used with the STRIPIT etchant; a six minute exposure at 95° C. was used with the NaOH etchant; and a 24 hour exposure at 95° C. was used with the HCl etchant.

The silane tested was an aqueous solution containing 0.1% γ-methacryloxypropyltrimethoxy silane marketed by Dow Corning of Midland, Michigan, under the designation Z6030, and by Union Carbide of Danbury, Connecticut, under the designation A174. To insure reaction on all sites of the bars, a heat cure at 100° C. for at least five minutes was undertaken. In general, exposure periods of about 3–30 minutes at temperatures ranging about 60°–150° C. have been found operable for curing, it being recognized that the longer times are required at temperatures within the cooler end of the temperature range. More extended periods may be utilized, but do not appear to significantly improve the cure and so are not economically desirable.

Curing at elevated temperatures is not mandatory, however. To illustrate, the silane can be cured at room temperature but, as can be appreciated, relatively long drying periods, e.g., up to about 24 hours and longer, will be required to insure sufficient curing to obtain very high strength levels, viz., greater than about 2000 psi.

The initial dental cement chosen was a modified PRISMA visible light curing (VLC) cement developed by L. D. Caulk Division, Dentsply International, Milford, Del. The modification involved the amount of filler present therein; viz., 49% instead of the standard 76%. The filler consisted of powdered Corning Code 7724 glass marketed by Corning Glass Works, Corning, N.Y., or powdered Raysorb T-3000 glass marketed by Esschem Co., Essington, Pa. Both glasses have compositions in the barium aluminoborosilicate field. This cement was selected because of its desirable characteristic of controlled rapid setting.

Table I provides a summary of the treatments applied to the test specimens and the results of this initial set of experiments. Also included is a control sample that was subjected to no treatment whatever. As noted above, the tabulated values, reported in terms of psi and representing the average of measurements conducted on four bars, were obtained after the specimens had been immersed in distilled water for 24 hours at 37° C.

TABLE I

| Grit Blast | Etch | Silane | Shear Bond |
|---|---|---|---|
| — | — | — | 80 |
| x | — | — | 235 |
| — | STRIPIT | — | 1437 |
| — | NaOH | — | 397 |
| — | HCl | — | 1155 |
| x | STRIPIT | — | 2059 |
| x | NaOH | — | 832 |
| x | HCl | — | 2632 |
| — | — | x | 478 |
| x | — | x | 2224 |
| x | STRIPIT | x | 2680 |
| x | NaOH | x | 3978 |
| x | HCl | x | 1771 |

Scanning electron micrographs taken of the surface of the samples clearly illustrated the changes wrought to the surface by the various treatments. For example, grit blasting with the 25 micron $Al_2O_3$ powder alone greatly increased the surface area, when compared with the original surface. The etching action of the STRIPIT removed the residual glass away from the surface crystals leaving a porous surface of crystals standing upright like rods, thereby significantly enhancing the mechanical interlocking properties of the sample. Scanning electron micrographs taken of the specimens subjected to the NaOH etching treatment indicated no significant changes in the surface, i.e., differential etching was lacking. The low shear bond strength reported in Table I bears out that circumstance. Thus, it was not until the alkali etch was combined with the silane treatment that a high shear bond strength was developed. Scanning electron micrographs taken of the bars subjected to the hot HCl etching treatment demonstrated that the surface crystals had been removed leaving a porous glassy surface layer.

As can be immediately recognized, the HCl etching treatment did not comply with the temperature restraints imposed above. The HCl concentration was increased and the time and temperature of the exposure decreased. A one hour exposure to concentrated HCl at 55° C. evidenced some removal of surface crystals, but the alteration of the surface by the action of STRIPIT was much more favorable. Accordingly, further experimentation with HCl solutions was ceased.

Whereas STRIPIT performed very well in etching the glass-ceramic bars, because of the recognized hazards associated with handling solutions containing free HF, a similarly operable, but less hazardous, HF-containing etchant would be preferred from a safety point of view. Aqueous solutions of $NH_4HF_2$ were examined and found to perform very satisfactorily. Whereas concentrations of $NH_4HF_2$ between about 5–20% can be operable, in subsequent work an aqueous solution containing 10% $NH_4HF_2$ was employed as an etchant.

In order to determine the long term stability of the bond developed, six treatments were selected and samples were prepared for measurement after storage in a bath of distilled water operating at 37° C. for periods of one day, two weeks, one month, three months, and six months, as well as processing through thermal cycling. This last practice involved cycling the samples 540 times between baths of distilled water operating at 10° C. and 50° C., with the samples remaining in each bath about one minute.

After being grit blasted, the samples were subjected to one of the following six treatments:

(a) a two minute immersion in STRIPIT;

(b) a two minute immersion in the 10% $NH_4HF_2$ solution;

(c) a one minute immersion in STRIPIT, drying, followed by a three minute immersion in Z6030, drying, and curing for five minutes at 100° C.;

(d) a three minute immersion in Z6030, drying, and curing for five minutes at 100° C.;

(e) a three minute immersion in Z6030; no heat cure; or (f) a one minute immersion in the 10% $NH_4HF_2$ solution, drying, followed by a three minute immersion in Z6030, drying, and curing for five minutes at 100° C.

In each instance the above-described modified PRISMA VLC dental cement was employed.

Each value reported in the following tables reflects the average of ten measurements.

TABLE II

| STRIPIT | |
|---|---|
| Test | Shear Strength (psi) |
| Thermal Cycling Water Storage | 1260 |
| 1 day | 2031 |
| 2 weeks | 1622 |
| 1 month | 1257 |
| 3 months | 1335 |
| 6 months | 1734 |

TABLE III

| $NH_4HF_2$ | |
|---|---|
| Test | Shear Strength (psi) |
| Thermal Cycling Water Storage | 1344 |
| 1 day | 1543 |
| 2 weeks | 1282 |
| 1 month | 1581 |
| 3 months | 1454 |
| 6 months | 1674 |

TABLE IV

| STRIPIT + Z6030 | |
|---|---|
| Test | Shear Strength (psi) |
| Thermal Cycling Water Storage | 2394 |
| 1 day | 2289 |
| 2 weeks | 1717 |
| 1 month | 2064 |
| 3 months | 1954 |
| 6 months | 2646 |

TABLE V

| Z6030 - Heat Cure | |
|---|---|
| Test | Shear Strength (psi) |
| Thermal Cycling Water Storage | 2474 |
| 1 day | 3049 |
| 2 weeks | 2367 |
| 1 month | 2498 |
| 3 months | 1954 |
| 6 months | 2227 |

TABLE VI

| Z6030 - No Heat Cure | |
|---|---|
| Test | Shear Strength (psi) |
| Thermal Cycling Water Storage | 1328 |
| 1 day | 2292 |
| 2 weeks | 3381 |
| 1 month | 3058 |
| 3 months | 2371 |
| 6 months | 2389 |

TABLE VII

| $NH_4HF_2$ + Z6030 | |
|---|---|
| Test | Shear Strength (psi) |
| Thermal Cycling Water Storage | 2766 |
| 1 day | 2983 |
| 2 weeks | 3236 |
| 1 month | 3055 |
| 3 months | 2025 |
| 6 months | 2497 |

Further studies were pursued utilizing a dental cement being developed experimentally. The cement can self-cure at room temperature, can be cured through exposure to visible light, or through a combination of the two practices.

Three treatments were selected and samples were prepared for measurement after storage in a bath of distilled water operating at 37° C. for periods of one day, one month, and six months, as well as processing through thermal cycling. In these examples this last procedure involved cycling the samples 6000 times between baths of distilled water operating at 10° C. and 50° C., with the samples remaining in each bath about one minute. The 6000 cycles have been calculated to represent an accelerated test equivalent to one year's actual use.

After being grit blasted, the samples were subjected to one of the following three treatments:

(a) a two minute immersion in the 10% $NH_4HF_2$ solution;

(b) a one minute immersion in the 10% $NH_4HF_2$ solution, drying, followed by a three minute immersion in Z6030, drying, and curing for five minutes at 100° C.; or (c) a one minute immersion in the 10% $NH_4HF_2$ solution, drying, followed by two successive three minute immersions in a solution containing equal parts of A174 and a solution consisting of 95% ethanol/5% acetic acid. The ethanol/acetic acid solution serves to chemically cure the silane. This manner of curing the silane was explored as a substitute for heat curing in order to provide a method for the dentist who might not have the capability of curing at 100° C.

Each of the reported values in Tables VIII–X reflects the average of ten measurements. The term "self cure" indicates that the dental cement was exposed to an environment of 37° C. for 15 minutes. The expression "dual cure" indicates that the dental cement was first subjected to high intensity visible light for 60 seconds and then rested in an ambient environment at 23° C. for at least 10 minutes.

TABLE VIII

| | $NH_4HF_2$ | | |
|---|---|---|---|
| | Self Cure | | Dual Cure |
| Test | Shear Strength (psi) | Test | Shear Strength (psi) |
| Thermal Cycling | 619 | Thermal Cycling | 1167 |
| Water Storage | | Water Storage | |
| 1 day | 1493 | 1 day | 1493 |
| 1 month | 1297 | 1 month | 1201 |
| 6 months | 1129 | 6 months | 961 |

TABLE IX

| | $NH_4HF_2$ + Heat Cured Z6030 | | |
|---|---|---|---|
| | Self Cure | | Dual Cure |
| Test | Shear Strength (psi) | Test | Shear Strength (psi) |
| Thermal Cycling | 1843 | Thermal Cycling | 2112 |
| Water Storage | | Water Storage | |
| 1 day | 2987 | 1 day | 3324 |
| 1 month | 3318 | 1 month | 3502 |
| 6 months | 2374 | 6 months | 2750 |

TABLE X

| | $NH_4HF_2$ + Chemically Cured A174 | | |
|---|---|---|---|
| | Self Cure | | Dual Cure |
| Test | Shear Strength (psi) | Test | Shear Strength (psi) |
| Thermal Cycling | 1223 | Thermal Cycling | 2073 |
| Water Storage | | Water Storage | |
| 1 day | 2100 | 1 day | 2502 |
| 1 month | 1887 | 1 month | 2893 |
| 6 months | 2343 | 6 months | 3055 |

As can be seen in Tables VIII–X, comparable shear strengths are secured whether the silane is heat cured or chemically cured. However, greater shear strengths are obtained when the cement is subjected to the dual cure practice rather than the single self cure. Nevertheless, in all instances the dual cure procedure produced bonds having shear strengths in excess of 1200 psi, the goal of the instant invention. It will be appreciated that the 95% ethanol/5% acetic acid solution is merely illustrative. Thus, the particular vehicle (ethanol) employed is not critical and the acetic acid concentration can range about 0.5–10%.

It was observed above that a critical requirement of the etching procedure was the need to protect the finished exterior surface of the dental appliance while the fitting surface is being treated. An immediate solution to that problem comprehends protecting the exterior surface with a layer of wax. Such practice, however, adds a step to the overall process and the removal of the wax is bothersome. We have found that the application of the etching solution to the dental appliance can be controlled by converting the solution into a flowable gel. Thus, the gel will flow sufficiently to permit ease of application to the dental appliance, but its viscosity will be high enough to prevent ready run off therefrom. In general, operable viscosities of the gel will range about 3000–8000 centipoises.

The method of gelling $NH_4HF_2$ is not vital so long as the reactivity of the $NH_4HF_2$ is not seriously impaired and the gellant does not deleteriously attack the surface of the dental appliance. In the following examples, NATRASOL 250 HR, a carboxymethylcellulose product marketed by Hercules, Inc. of Wilmington, Delaware, comprised the gellant.

Three aqueous gels containing 10% $NH_4HF_2$ were prepared exhibiting viscosities of 4000, 5000, and 6000 centipoises. Each gel was evaluated for handling characteristics and for etching effectiveness. The latter capability was deduced from shear bond strength measurements and by comparisons of scanning electron micrographs taken of the bar surfaces with those taken of surfaces etched with the aqueous 10% $NH_4HF_2$ solutions.

In like manner to the examples reported above, grit blasted bars of the same glass-ceramic material were employed in the following treatments. The gelled etchant was applied thereto in the manner described below:

(1) using a small brush, the gelled acid was quickly spread over the surface of the bar in a layer of at least 1 mm and, commonly, 2–3 mm thickness;

(2) after two minutes' residence time, the etchant was washed off with pressurized water; and then (3) the surface was dried.

In the examples recorded in Table XI, the experimental dental cement described above subjected to the above-described dual cure procedure constituted the bond. The gels are tabulated in terms of their viscosities and each value of shear bond strength reflects an average of 10 measurements after immersion for one day in a bath of distilled water operating at 37° C.

TABLE XI

| Gelled $NH_4HF_2$ | |
|---|---|
| Gel | Shear Strength (psi) |
| 6000 centipoises | 1580 |
| 5000 centipoises | 1458 |
| 4000 centipoises | 1614 |

A comparison of those values with the 1 day value reported in Table VIII (1493 psi) demonstrates a close similarity to the results obtained with the 10% $NH_4HF_2$ solution. Scanning electron micrographs of the etched surface also showed a morphology quite like that observed with the $NH_4HF_2$ solution etch.

Whereas the gelled etchant having the lowest viscosity, viz., 4000 centipoises, exhibited the best handling characteristics, viscosities less than about 3000 centipoises become too fluid for easy application.

Thereafter, in like manner to the examples set out above, grit blasted bars of the same glass-ceramic material were subjected to the following nine sequences of treatments:

SEQUENCE A (a) an aqueous solution containing 10% $NH_4HF_2$ was blended with NATRASOL 250 HR to yield a gel exhibiting a viscosity of about 4000 centipoises and that gel was brushed onto the surface of the bars to apply a coating thereon of about 2–3 mm thickness;
(b) after a residence time of about 2 minutes, the gelled etchant was washed off with pressurized water;
(c) the bars were thereafter immersed for 3 minutes in A-174 solution;
(d) the bars were removed from the A-174 solution and allowed to rest in the ambient environment for 15 minutes; and then
(e) the experimental dental cement referred to above was applied as previously described and subjected to the "dual cure" procedure explained above.

SEQUENCE B

Each of the above five steps of Sequence A was employed. However, in Step (d) a rest period in the ambient environment for 24 hours was employed.

SEQUENCE C

Each of the above five steps of Sequence A was employed with a rest period of 48 hours in the ambient environment being utilized in Step (d).

SEQUENCE D (a) an aqueous solution containing 10% $NH_4HF_2$ was blended with NATRASOL 250 HR to produce a gel demonstrating a viscosity of about 4000 centipoises and that gel was brushed onto the surface of the bars to provide a layer thereon of about 2–3 mm thickness;
(b) after a dwell period of about 2 minutes, the gelled etchant was washed off with pressurized water and the bars dried for about 5 minutes in an oven operating at 100° C.;
(c) the bars were immersed for 3 minutes in A-174 solution;
(d) the bars were removed from the A-174 solution and dried for about 5 minutes in an oven operating at 100° C.;
(e) the bars were removed from the oven and allowed to rest in the ambient environment for about 15 minutes; and subsequently
(f) the experimental dental cement discussed above was applied as reviewed above and subjected to the "dual cure" practice described above.

SEQUENCE E

Each of the above six steps of Sequence D was followed. However, in Step (e) a rest period in the ambient environment of 24 hours was employed.

SEQUENCE F

Each of the above six steps of Sequence D was employed, but a rest period of 48 hours in the ambient environment was utilized in Step (e).

SEQUENCE G

Each of the above six steps of Sequence D was employed, but a drying period of 30 minutes in an oven operating at 100° C. was utilized in Step (d).

SEQUENCE H

Each of the above six steps of Sequence E was employed, but a drying period of 30 minutes in an oven operating at 100° C. was utilized in Step (d).

SEQUENCE I

Each of the above six steps of sequence F was employed, but a drying period of 30 minutes in an oven operating at 100° C. was utilized in Step (d).

Each of the values reported in Table XII comprises an average of six measurements of shear strength (psi) determined after immersion of the samples for 24 hours in a water bath operating at 37° C.

TABLE XII

| Samples | Shear Strength |
| --- | --- |
| Sequence A | 1630 |
| Sequence B | 2452 |
| Sequence C | 2039 |
| Sequence D | 2119 |
| Sequence E | 2599 |
| Sequence F | 2693 |
| Sequence G | 2436 |
| Sequence H | 2424 |
| Sequence I | 2352 |

Several conclusions can be drawn from Table XII:

First, in all instances the shear strengths exceeded the minimum level desired;

Second, drying of the bars after removing the etchant gel therefrom is not mandatory, but careful washing of the bars prior to contact with the silane should be practiced;

Third, heat curing of the silane is not necessary, although rather lengthy residence periods at ambient temperature are required to insure sufficient curing such as to obtain high strength values, i.e., greater than 2000 psi;

Fourth, extended periods of heat curing the silane have essentially no effect upon the ultimate strength levels obtained; and Fifth, the strength values secured through the use of the gelled etchant are comparable to those resulting from the use of a liquid etchant.

We claim:

1. A method for developing a bond exhibiting a shear strength in excess of 1200 psi between dental cements and etched fitting surfaces of dental appliances prepared from glass-ceramic materials wherein the exterior surface of the appliance is protected during the etching of the fitting surface, said method comprising the steps of:

(a) contacting at a temperature not exceeding about 150° F. the fitting surface of a dental appliance prepared from a glass-ceramic material consisting essentially, expressed in terms of weight percent on the oxide basis, of 10–18% $K_2O$, 14–19% $MgO$, 0–2% $Al_2O_3$, 0–7% $ZrO_2$, 55–65% $SiO_2$, and 4–9% F with an etchant in flowable gel form for a period of time adequate to promote differential etching of said fitting surface whereby the glass phase is removed to produce a tortuous path around the crystals of said glass-ceramic materials to provide a bonding surface having a depth of about 0.25–5 microns with holes resulting from said etching having diameters of about 0.35–10 microns dispersed throughout, said etchant consisting of an aqueous 5–20% $NH_4HF_2$ solution and said gel exhibiting a viscosity between 3000–8000 centipoises;

(b) removing the gelled etchant from the fitting surface of the appliance;

(c) contacting the etched surface of the appliance with a silane solution for a period of time adequate to promote impregnation of the holes in said surface;

(d) removing the excess silane solution from the etched surface and drying and curing the residual silane; and thereafter (e) applying a dental cement to the etched surface and curing the cement in place.

2. A method according to claim 1 wherein said fitting surface of said dental appliance is contacted with said flowable gel for at least one minute.

3. A method according to claim 1 wherein said etched surface of said dental appliance is contacted with said silane solution for at least three minutes.

4. A method according to claim 1 wherein said silane solution consists of an aqueous solution containing 0.1% γ-methacryloxypropyltrimethoxy silane.

5. A method according to claim 1 wherein said silane is heat cured by exposure to temperatures between about 60°–150° C. for times between about 3–30 minutes.

6. A method according to claim 1 wherein said silane is cured by exposure to ambient temperature for a period of time of at least 24 hours.

7. A method according to claim 1 wherein said silane is chemically cured by reaction with a 0.5–10% solution of acetic acid.

8. A method according to claim 1 wherein said dental appliance is a veneer.

* * * * *